United States Patent [19]

Herman et al.

[11] 4,314,067
[45] * Feb. 2, 1982

[54] MONOMERIC COMPOUNDS HAVING VINYL AND IMIDAZOLIDIN-2-ONE TERMINAL GROUPS

[75] Inventors: Frederick L. Herman, Allentown; Dale D. Dixon, Kutztown, both of Pa.

[73] Assignee: Air Products and Chemicals, Inc., Allentown, Pa.

[*] Notice: The portion of the term of this patent subsequent to Sep. 5, 1995, has been disclaimed.

[21] Appl. No.: 883,554

[22] Filed: Mar. 6, 1978

Related U.S. Application Data

[63] Continuation-in-part of Ser. No. 709,677, Jul. 29, 1976, Pat. No. 4,111,877.

[51] Int. Cl.³ .................. C07D 233/36; C07D 233/34
[52] U.S. Cl. ..................... 548/320; 544/160; 544/169; 544/316; 546/245; 260/326.4; 564/30; 564/59; 564/60
[58] Field of Search ............... 548/320; 544/160, 169, 544/316; 546/245; 260/326.4

[56] References Cited

U.S. PATENT DOCUMENTS

| | | | |
|---|---|---|---|
| 2,840,546 | 6/1958 | Yost | 548/320 |
| 3,014,042 | 12/1961 | Mantz | 548/320 |
| 3,021,338 | 2/1962 | Bortnick | 548/320 |
| 3,024,246 | 3/1962 | Goodman, Jr. | 548/320 |
| 3,196,152 | 7/1965 | Wright, Jr. et al. | 548/320 |
| 4,104,220 | 8/1978 | Sims | 548/320 |

*Primary Examiner*—Henry R. Jiles
*Assistant Examiner*—Natalia Harkaway
*Attorney, Agent, or Firm*—E. Eugene Innis; Russell L. Brewer

[57] ABSTRACT

Polymerizable monomeric compounds corresponding to the general formula

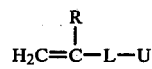

wherein R is H or $CH_3$, U designates a cyclic or acyclic ureido or thioureido group and L designates a selected linking structure. The linking structure L may contain one or more oxy (ether), amino, amido, or carbonyl groups provided that any carbonyl group (CO) present is not directly attached to U or to an ethylenic carbon atom nor is such ethylenic carbon atom directly attached to a nitrogen atom. Representative examples include compounds corresponding to the formulae:

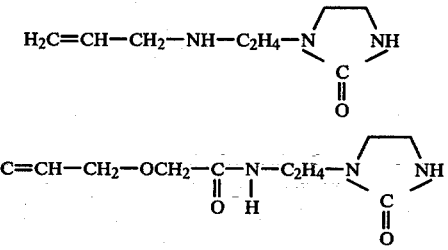

3 Claims, No Drawings

MONOMERIC COMPOUNDS HAVING VINYL AND IMIDAZOLIDIN-2-ONE TERMINAL GROUPS

CROSS-REFERENCE TO RELATED APPLICATIONS

The present application is a continuation-in-part of our application Ser. No. 709,677 filed July 29, 1976 now U.S. Pat. No. 4,111,877.

Aqueous emulsions containing compounds of the present inventions and coating compositions formed therewith are claimed in companion application having U.S. Ser. No. 873,813 now U.S. Pat. No. 4,151,142, and entitled "Wet Adhesion Emulsions for Paints and Coating Compositions."

BACKGROUND OF THE INVENTION

1. Field of the Invention

This invention relates to generally polymerizable monomeric compounds containing a terminal ureido group. More particularly, the invention is concerned with novel compounds having at one end thereof a cyclic or acyclic ureido group and at the other end a vinyl group, the terminal groups being connected through a selected linking structure as hereinafter described. The novel compounds of the invention can be designated by the general structural formula:

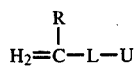  (I)

wherein R is H or $CH_3$, U designates a cyclic or acyclic ureido or thioureido group and L designates the linking structure, as hereinafter described.

2. Prior Art

There are disclosed in the prior art various monomeric compounds containing a ureido group at one end and an unsaturated ethylenic group at or near the opposite end, which unsaturated group may be the residue of an unsaturated mono- or di-carboxylic acid. Thus, the U.S. Pat. Nos. 2,881,155 and 2,881,171, there are described monomeric polymerizable compounds containing at one end a cyclic ureido group, and at the other end an acrylic or methacrylic acid radical linked through an alkyl amido group. These compounds correspond to the general structural formula

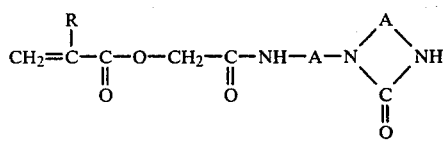  (II)

wherein R is H or $CH_3$ and A is an alkylene group having 2 or 3 carbon atoms.

Compounds of this type are prepared, for example, by condensing N-$\beta$- aminoethyl-N-N'-ethyleneurea with an ester of an alpha haloacetic acid and then reacting the obtained intermediate with a salt of acrylic or methacrylic acid. The obtained compounds are capable of undergoing addition polymerization and condensation reactions.

Another type of compound containing a cyclic ureido structure at one end and at the other end the residue of an unsaturated dicarboxylic acid is described in U.S. Pat. No. 2,980,652; such compounds correspond generally to the formula:

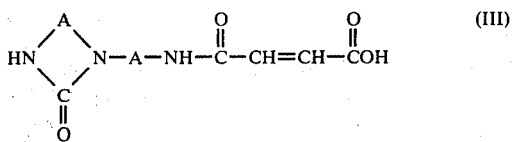  (III)

Compounds of this type are also stated to be susceptible to both addition polymerization, by virtue of their unsaturation, and to condensation reactions by virtue of the heterocyclic nitrogenous rings.

Instead of condensing the N-aminoalkyl urea with an unsaturated dicarboxylic acid, a monocarboxylic acid, such as crotonic acid, is employed in U.S. Pat. No. 3,369,008 forming compounds of the general formula

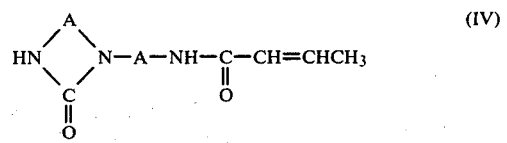  (IV)

By reacting the anhydride of a dicarboxylic acid with the N-hydroxyalkyl derivative of a cyclic urea, ester compounds are formed according to U.S. Pat. No. 3,194,792. These compounds correspond generally to the formula

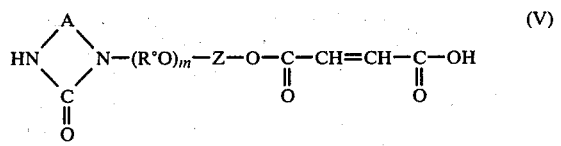  (V)

(m=zero to 9)
$Z=C_2$ to $C_8$ alkylene group
$R^o=C_2$ to $C_3$ alkylene group

The foregoing types of compounds are stated to be useful for one or more of the following purposes: as plasticizers for vinyl and acrylic resins and as anti-static agents; they may be reacted to form copolymers and interpolymers with monoethylenically unsaturated compounds, useful as warp sizes and for improving wet strength of paper; such copolymers also provide valuable coating compositions and bases for water-base paints, as well as binders for non-woven fabrics among other noted uses. Other suggested uses for certain of these compounds include the formation with various resin components of polymeric compositions having improved adhesion properties when employed in paints and coating compositions, particularly as applied to metals, glass and plastics.

A wide variety of monomers containing a ureido group of straight chain or cyclic type are disclosed in U.S. Pat. No. 3,300,429, including certain of those hereintofore described. According to that patent, improved coating and impregnating compositions are formed by admixing certain water insoluble addition polymers (1), such as vinyl ester or acrylic polymers, with a low molecular weight soluble ammonium salt of certain copolymers of ethylenically unsaturated carboxylic acids (2), and with a specified surfactant; when at least one of the components (1) or (2) comprises polymerized monomer units containing a ureido group.

These coating compositions in the form of aqueous polymer dispersions and water base paints are stated to possess improved adhesion and penetration properties such as in their application to porous substrates including wool, textiles and non-woven fabrics as well as in their application to powdery or chalky surfaces.

In our copending patent application Ser. No. 709,677 filed July 29, 1976, there are described novel cyclic ureido monomers terminating at the opposite end in the residue of an allyl or methallyl ester as in

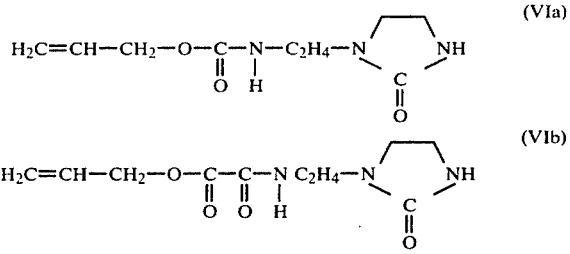

The compounds of said copending application, in contrast to the known cyclic ureido derivatives of the prior art, are characterized in that the carbonyl group in the chain linking the amino nitrogen of the N-aminoalkyl urea to the terminal ethylene group, is not directly attached to an ethylenic carbon atom.

In copending U.S. patent application Ser. No. 709,916 filed July 29, 1976, the synthesis of novel allyl succinamic ureido compounds is described. These compounds as well as those described in the companion copending application Ser. No. 709,677, are shown to be particularly useful as functional comonomers for imparting improved wet adhesion properties to emulsion systems containing vinyl ester polymers employed in paints and coating compositions. Other suggested uses for the described monomers of the aforesaid copending patent applications include: their use as such or as intermediates in resin modifiers, and as plasticizers, textile sizes, textile softeners, antistatic agents and wet strength paper resins.

SUMMARY OF THE INVENTION

Among the objects of the present invention is to extend the variety and compass of ureido monomers useful for the various purposes hereinbefore described, by providing additional novel compounds and methods for their synthesis.

The novel compounds of the present invention correspond to the general formula

wherein R is H or $CH_3$, U designates a cyclic or acyclic ureido or thioureido group and L designates a selected linking chain connecting a ureido nitrogen to the olefinic carbon of the ($-C=CH_2$) terminal group at the opposite end of the chain. The linking chain L, for example, may contain one or more oxy (ether), amino, amido or carbonyl groups, provided that any carbonyl group (CO) present is not directly attached to U or to an ethylenic carbon atom nor is an ethylenic carbon directly attached to a nitrogen atom. The ureido terminal group —U— may be acyclic, corresponding to the structure

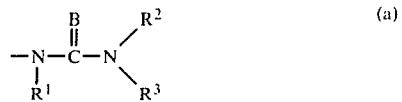

in which B is an oxygen or sulfur atom, and $R^1$, $R^2$ and $R^3$ each separately is hydrogen, alkyl, aryl, hydroxyalkyl or alkoxy alkyl, or $R^2$ and $R^3$ may form a cyclic structure by being part of a piperidine, pyrrolidine or morpholine structure; or the ureido group may be cyclic, corresponding to the structure

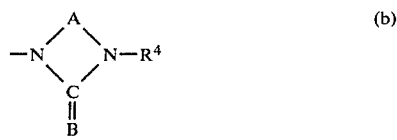

wherein B is an oxygen or sulfur atom, $R^4$ is hydrogen, alkyl, aryl, hydroxyalkyl or alkoxyalkyl; and A is an alkylene group of 2 to 3 carbon atoms, such as $-CH_2-CH_2-$, $-CH_2-CH_2-CH_2$, or $-H_2C-CH(CH_3)-$.

DESCRIPTION OF THE PREFERRED EMBODIMENTS

Illustrative examples among the types of linking structures L comprised in the novel compounds of the invention corresponding to formula I above, include the following:

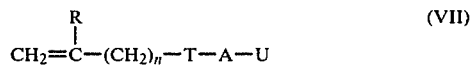

wherein R, $R^1$, A and U are as defined above, T is oxygen or

and n is an integer from 1 to 9. L in this compound then is $-(CH_2)_n-T-A-$. A specific example of such compound is represented by the formula

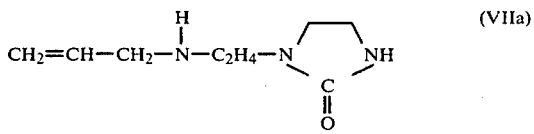

A further group of compounds are those represented by the general formula

wherein G is $CH_2NR^1$ or $CH_2$, T is oxygen or $NR^1$ and the other symbols are as above defined. In this example L is $$-G-\underset{\underset{B}{\|}}{C}-T-A-.$$

Specific examples of such compounds are those corresponding to the formulae $$CH_2=CH-CH_2-\underset{H}{N}-\underset{\|}{\overset{O}{C}}-\underset{H}{N}-C_2H_4-N\underset{\underset{O}{\|}}{\diagdown}NH \quad \text{(VIIIa)}$$

$$CH_2=CH-CH_2-O-\overset{O}{\underset{\|}{C}}-O-C_2H_4-N\underset{\underset{O}{\|}}{\diagdown}NH \quad \text{(VIIIb)}$$

$$H_2C=CH-CH_2-O-\overset{O}{\underset{\|}{C}}-\underset{\underset{}{\overset{CH_3}{|}}}{N}-C_2H_4-N\underset{\underset{O}{\|}}{\diagdown}NH \quad \text{(VIIIc)}$$

A further type of useful compounds is represented by the general formula $$CH_2=\overset{R}{\underset{|}{C}}-D-\overset{O}{\underset{\|}{C}}-T-A-U \quad \text{(IX)}$$

wherein D is $(CH_2)_n$ or $CH_2-T-(CH_2)_n-$. In this group L is $$-D-\underset{\underset{O}{\|}}{C}-T-A-.$$

Particular examples of such compounds include those represented by the formulae $$CH_2=CH-CH_2-\underset{\underset{O}{\|}}{C}-\overset{H}{\underset{|}{N}}-C_2H_4-N\underset{\underset{O}{\|}}{\diagdown}NH \quad \text{(IXa)}$$

$$CH_2=CH-CH_2O-(CH_2)_3-\underset{\underset{O}{\|}}{\overset{}{C}}-\underset{\underset{H}{|}}{N}-C_2H_4-N\underset{\underset{O}{\|}}{\diagdown}NH \quad \text{(IXb)}$$

$$CH_2=CH-CH_2O-CH_2-\underset{\underset{O}{\|}}{\overset{}{C}}-\underset{\underset{H}{|}}{N}-C_2H_4-N\underset{\underset{O}{\|}}{\diagdown}NH \quad \text{(IXc)}$$

A further group of useful compounds is represented by the general formula $$CH_2=\overset{R}{\underset{|}{C}}-J-\overset{O}{\underset{\|}{C}}-E-U \quad \text{(X)}$$

wherein E represents an alkylene group of 1 to 10 carbon atoms and J is $CH_2O-$, $CH_2 NR^1-$, or an oxygen atom. In this example, L is $$-J-\underset{\underset{O}{\|}}{C}-E-.$$

Illustrative examples of such compounds include those represented by the formulae $$CH_2=\overset{H}{\underset{|}{C}}-CH_2O-\overset{O}{\underset{\|}{C}}-C_2H_4-N\underset{\underset{O}{\|}}{\diagdown}NH \quad \text{(Xa)}$$

$$CH_2=\underset{\underset{H}{|}}{C}-O-\underset{\underset{O}{\|}}{C}-CH_2-N\underset{\underset{O}{\|}}{\diagdown}NH \quad \text{(Xb)}$$

Another group of useful compounds is that represented by the general formula $$CH_2=\overset{R}{\underset{|}{C}}-J-\overset{O}{\underset{\|}{C}}-E-T-A-U \quad \text{(XI)}$$

In this class of compounds, L is $$-J-\underset{\underset{O}{\|}}{C}-E-T-A-.$$

Illustrative examples of such compounds are:

$$CH_2=CH-O-\overset{O}{\underset{\|}{C}}-CH_2-NH-C_2H_4-N\underset{\underset{O}{\|}}{\diagdown}NH \quad \text{(XIa)}$$

$$CH_2=CHCH_2-O-\overset{O}{\underset{\|}{C}}-C_2H_4-NH-C_2H_4-N\underset{\underset{O}{\|}}{\diagdown}NH \quad \text{(XIb)}$$

A further group of such compounds is that represented by the general formula $$CH_2=\overset{R}{\underset{|}{C}}-J-\overset{O}{\underset{\|}{C}}-E-\overset{O}{\underset{\|}{C}}-T-A-U \quad \text{(XII)}$$

In this group L is $$-J-\underset{\underset{O}{\|}}{C}-E-\underset{\underset{O}{\|}}{C}-T-A-.$$

A specific example of compounds coming within this group is that represented by the formula:

$$CH_2=CH-CH_2O-\overset{O}{\underset{\|}{C}}-C_2H_4-\overset{O}{\underset{\|}{C}}-O\ C_2H_4-N\underset{\underset{O}{\|}}{\diagdown}NH \quad \text{(XIIa)}$$

SYNTHESIS OF HCl SALT OF N-β-(ALLYLAMINO) ETHYL ETHYLENEUREA (FORMULA VIIa)

To a reaction vessel containing 285.5 parts by weight of allylamine, there were added 148.04 parts of N-(β-chloroethyl)-N,N¹-ethyleneurea and 750 parts distilled water. A slight exotherm was observed (temperature rise about 16° C.).

Heating was commended with stirring, and an initial reflux temperature of 87.5° C. was observed. The reactants were permitted to reflux overnight, after which the contents were transferred to a concentrating vessel and heated at about 75° C. to remove water and excess allyl amine.

A mass of yellow waxy material was obtained. This product was taken up in absolute ethanol (350 parts product per 237 parts alcohol) and to the resulting hot mixture there was added 630 parts by weight of ethyl acetate and the mixture set aside to cool slowly. Crystals of the hydrochloride salt of compound VIIA were filtered off from the cooled mixture and dried in a vacuum oven at room temperature.

Actual yield obtained was 85.11% of theory. The crystalline product had a melting point of 151.5°–152.5° C.

| | ELEMENTAL ANALYSIS | | |
|---|---|---|---|
| | C | H | N |
| Actual % | 45.95 | 7.99 | 19.94 |
| Theor. % | 46.74 | 7.78 | 20.44 |

Instead of reacting the chloroethyl urea compound with the allylamine, the same product can be obtained by reacting the 2-aminoethyl ethyleneurea with allyl halide. If one employs as reactant with the ureido amine, the isomeric 1-halo-2-methyl-2-propene compound, corresponding compounds are obtained terminating in the

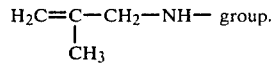

group.

PREPARATION OF ALLYL(β-1-ETHYLENEUREIDO) ETHYL CARBONATE (FORMULA VIIIb)

In a reaction vessel there were mixed

| | parts by weight (pbw) |
|---|---|
| N-β-(hydroxyethyl)-N,N¹-ethyleneurea | 130 |
| Methylene chloride | 1325.5 |
| Triethylamine | 126.31 |

To the resulting mixture there was added dropwise 150.6 parts allyl chloroformate while maintaining the temperature at 10°–15° C. The addition took about 1.5 hours.

The mixture began to reflux at about 45° C., and was continued overnight. It was then filtered with suction and the filtrate containing the product was concentrated under vacuum. The last traces of solvent were removed by vacuum pumping overnight with heating to 50° C. Actual yield was 88.7% of theory.

| | ELEMENTAL ANALYSIS | | |
|---|---|---|---|
| | C | H | N |
| % theory | 50.49 | 7.51 | 13.08 |
| % actual | 51.54 | 6.53 | 12.63 |

SYNTHESIS OF N-(β-1-ETHYLENEUREIDO) ETHYL ALLYLOXYACETAMIDE (FORMULA IXc)

The reactants comprised:

| | parts by weight (pbw) |
|---|---|
| N-(β-aminoethyl)-N,N'-ethyleneurea | 71 |
| Allyl allyloxyacetate | 86.23 |
| Acetonitrile | 157.14 |

These were added one after another to a reaction vessel and the mixture stirred for about 2 hours at room temperature. A TLC (thin layer chromotography) plate was run on the mixture which indicated that some product was formed.

The reaction was maintained at 50° for about 17 hours. The TLC plate was again run on the mixture which indicated further product formation.

The product was heated for an additional three hours, then cooled and filtered to remove the precipitated impurities. The filtrate was stripped of acetonitrile and allyl alcohol by rotary evaporation. A clear yellow oil remained which solidified on standing at room temperature. The obtained solid material was recrystallized from ethanol/ethyl ether and had a melting point of 73°–74° C. The actual yield was 45.16% of theory.

PRODUCTION OF ALLYL N-METHYL-N-β-(1-ETHYLENEUREIDO) ETHYL CARBAMATE (FORMULA VIIIc)

In a reaction vessel there were mixed

| | parts by weight (pbw) |
|---|---|
| N-(β-Methylaminoethyl)-N,N'-ethyleneurea | 18 |
| Methylene chloride | 99.4 |
| Sodium hydroxide (30% aqueous solution) | 143. | and the mixture stirred until a clear solution was obtained. To this solution there was added dropwise with cooling 12 parts of allyl chloroformate, keeping the temperature between 15°–20° C.

The reaction mixture was then stirred at room temperature for about an hour and let stand to permit the product to separate into layers. The bottom layer comprising the methylene chloride solution was dried over anhydrous magnesium sulfate. Following filtration to remove the magnesium sulfate, the methylene chloride solvent was stripped off at about 30° C. under vacuum. The product was obtained at 87.27% of theoretical yield.

It was confirmed by TLC that there was only one component in the reaction product and the structure was confirmed by NMR (nuclear magnetic resonance spectroscopy).

| ELEMENTAL ANALYSIS | | | |
|---|---|---|---|
| | C | H | N |
| Theoretical % | 52.88 | 7.48 | 18.5 |
| Actual % | 51.61 | 7.78 | 18.14 |

The compounds of the invention may be incorporated in emulsion systems containing acrylic, vinyl ester or other pigmented or non-pigmented aqueous emulsion systems useful in paints and coatings in the manner described in the aforesaid copending applications.

EXAMPLE 1

The following specific example illustrates the polymerization of the ureido compound of the type described within a commercial interpolymer system comprising vinyl acetate, vinyl chloride, ethylene and maleic acid.

To a pressure vessel, one charges:

| | parts by weight (pbw) |
|---|---|
| Vinyl acetate | 4540 |
| (a) Triton X-301 (20%) | 1040 |
| (b) Igepal CO-730 | 416 |
| (c) Siponate DS-10 | 208 |
| Sodium vinyl sulfonate (25%) | 98 |
| Potassium persulfate | 300 |
| Ferrous salt | 1.5 |
| Water | 8170 |

(a) Anionic surfactant; sodium salt of an alkaryl polyether sulfate.
(b) Nonionic surfactant; nonylphenoxy-poly (ethyleneoxy) ethanol comprising 75% ethylene oxide.
(c) Anionic surfactant; purified dodecyl benzene sodium sulfonate.

The agitated vessel contents initially show a pH of 3.2.

The kettle contents are purged with $N_2$ and agitated at 150 rpm. Upon heating to 46° C., the charge is pressurized to 900 psi (63.28 kg/cm$^2$) with ethylene. Polymerization then is initiated with a 2.0% Discolite solution and followed by simultaneous addition to the kettle of the following compositions in 5 delays.

In the first delay, the initiator is introduced over a period of eight hours and is composed of:

| Delay 1 | pbw |
|---|---|
| (d) Discolite | 200 |
| water | 4600 |
| NH$_4$OH (28%) | 200 |

(d) Sodium formaldehyde sulfoxylate.

The second and third delays are introduced during a three hour period. These comprise:

| Delay 2 | Delay 3 |
|---|---|
| 4540 parts vinyl acetate | 9090 parts vinyl chloride |

The fourth and fifth delays are introduced during a four hour period. These comprise:

| Delay 4 | pbw | Delay 5 | pbw |
|---|---|---|---|
| Maleic acid (29% sol) | 664 | ureido cmpd. VIIIc | 363 |
| sodium vinyl sulfonate | 293 | water | 1816 |
| water | 2227 | | |

The polymerization temperature is maintained at 50° C. with a jacket temperature of 23°–50° C. The kettle pressure is maintained at about 960 psi (67.5 kg/cm$^2$) throughout the delays. At the end of the delays, the vinyl acetate free monomer content generally is less than 0.5% and the final emulsion has a solids content of 53.4%. The final pH is adjusted to 5.0.

EXAMPLE 2

An example for preparation of another emulsion system comprising a copolymer of vinyl acetate with ethylene and maleic acid is as follows.

There is charged to a pressure vessel

| | parts by weight (pbw) |
|---|---|
| Vinyl acetate | 1,907 |
| (e) Igepal CO 887 | 1,218 |
| (f) Igepal CO 630 | 426 |
| Sodium vinyl sulfonate (25%) | 158 |
| Polysodium vinyl sulfonate (25%) | 171 |
| Potassium persulfate | 80 |
| Fe++ | 0.3 |
| Water | 18,160 |

(e) Nonyl phenoxypoly (ethyleneoxy) ethanol comprising 86% ethylene oxide.
(f) Nonyl phenoxypoly (ethyleneoxy) ethanol comprising 65% ethylene oxide.

The stirred mixture has an initial pH of about 3.2.

The kettle contents are stirred at 150 rpm, purged with nitrogen, and then pressurized to 570 psi (=40 kg/cm$^2$) while heating to 50° C. Polymerization is initiated with a 50% solution of Discolite and added to the kettle simultaneously over a four hour period, are four delays as follows:

| | pbw | | pbw |
|---|---|---|---|
| Delay 1 | | Delay 2 | |
| Vinyl acetate | 19,749 | Maleic anhyd. | 115 |
| Triallyl cyanurate | 8,898 | Sodium vinyl sulfonate (25%) | 173 |
| | | Pot. persulfate | 58 |
| | | Water | 922 |
| Delay 3 | | Delay 4 | |
| Discolite | 250 | Ureido compound VIIIc | 363 |
| NH$_4$OH (28%) | 150 | Water | 4631 |
| Water | 5,000 | | |

The polymerization temperature is maintained at 50° C. with a jacket temperature of 43° C. and ethylene pressure of 570 psi (=30 kg/cm$^2$) during the course of the delays. At the end of the delays, and when the vinyl acetate free monomer content is less than 0.5%, the emulsion is cooled to ambient temperature and transferred to a degasser. The emulsion contains 50% solids.

EXAMPLE 3

A further example of an emulsion system comprising a copolymer of vinyl acetate and butyl acrylate made up for a semigloss paint which shows particularly good wet adhesion properties with addition of selected ureido compounds, is formulated as follows:

Into a jacketed reaction vessel there is charged

| | pbw |
|---|---|
| Hydroxyethyl cellulose | 0.45 |
| Alkyl phenoxy poly (oxyethylene) ethanols | 13.7 |
| Ferrous salt | (trace) |
| De-ionized water | 380 |

The vessel and contents are purged with nitrogen while heated to 65° C. and stirred. Then, there are added to the vessel at delayed intervals the three following mixtures

| Mixture 1 | pbw |
|---|---|
| Vinyl acetate | 415.2 |
| Butyl acrylate | 67.5 |
| *Pluronics | 15.6 |
| t-Butyl peroxide (70%) | 0.7 |

| Mixture 2 | pbw |
|---|---|
| Sodium formaldehyde bisulfite | 0.2 |
| Sodium benzoate | 0.6 |
| De-ionized water | 8.2 |

| Mixture 3 | pbw |
|---|---|
| Ureido compound VIIa | 2.4 |
| De-ionized water | 72.0 |

*Pluronics are non-ionic block polymers comprising polyalkylene derivatives of propylene glycol terminating in hydroxyl.

The first and third mixtures are added over a two hour period while the second is added during a fifteen minute period. The polymerization mixture is maintained at 65° C. After addition of the second mixture is completed, there is further added a solution of 0.6 parts of sodium formaldehyde bisulfite in 18.1 parts de-ionized water until polymerization is completed. The emulsion then is cooled to ambient temperature. It has a pH of about 5.2 and contains about 55.4% solids. Addition of a pigment dispersion to the emulsion provides a semigloss paint with outstanding wet adhesion.

EXAMPLE 4

An example of an all acrylic emulsion to which improved wet adhesion properties is conferred by incorporation of the selected ureido compounds is formulated as follows.

To a reaction vessel there is added:

| | pbw |
|---|---|
| Igepal CO 887 | 61 |
| Igepal CO 630 | 31.3 |
| Fe++ | trace |
| Water | 935.8 |

The contents of the vessel are stirred at 120 rpm and heated to 65° C. under a nitrogen purge. Then there are added to the reaction vessel over a two hour period, three delays, as follows:

| | pbw |
|---|---|
| Delay 1 | |
| Ethyl acrylate | 480 |
| Methyl Methacrylate | 320 |
| t-butyl hydroperoxide (70%) | 1.4 |
| Delay 2 | |
| Sodium formaldehyde sulfoxylate | 1.5 |
| Sodium benzoate | 1.1 |
| Deionized water | 48.5 |
| Delay 3 | |
| Ureido compound VIIa | 8.0 |
| Deionized water | 92 |

The polymerization temperature is maintained at 65°–66° C. with a cooling jacket temperature of 60° C. At the end of the delays, and when there is no visible reaction exotherm, there is added to the emulsion 2.0 parts of sodium formaldehyde sulfoxylate and 1 part of t-butyl hydroperoxide (70%) mixed with 10 parts water. The obtained emulsion has about 44.4% solids and a pH of about 5.1.

The foregoing emulsion when put into a standard semigloss paint formulation, passes the cut film wet adhesion test described below.

The cut film test employed is a standard procedure for testing wet adhesion to a surface of semi-gloss paint as set out in Federal Specification TT-P-001511, paragraph 4.3.9 (GSA-FSS). In this test a panel is painted with an alkyd enamel of specified composition and permitted to dry under specified conditions. The test paint is then applied over the alkyd surface and dried. A cut is then made longitudinally through the center of the test film and the panel scrubbed under water at a specified rate of brush travel. To pass this test, there must be no loss of adhesion between the test paint and the alkyd undercoat and no wearing through to the undercoat in fewer than 5,000 cycles.

In the recut test, a second cut is made perpendicular to the first on the test film. To pass this test it is required that there be no adhesion failure between the test paint and the alkyd undercoat in fewer than 1000 cycles of under water brushing.

In the "floating board" test, the composition to be tested is applied over a dry glossy alkyd-painted plane board surface and dried. A one-inch section of the surface is scored by cross-hatching with parallel cuts vertical and horizontal 1/10–⅛ inch apart. An adhesive tape is applied to the dry scored surface and the relative amounts of the surface film peeled off by the adhesive observed. The board is again similarly scored and then floated face down on a water bath to wet the scored surface and the adhesive tape procedure repeated, again observing the amount of painted surface removed.

A representative number of ureido compounds were each incorporated into an emulsion system for testing of wet adhesion properties. The systems tested contained 0.75% of the ureido compound. Other amido compounds were also included in these tests as well as a control free of additive.

The results of the tests are shown in Tables 1 and 2 below, respectively, on the cut film and floating board tests.

The emulsion systems employed in all of the tests reported in Tables 1 and 2 were similarly prepared except for the particular ureido or amido compound employed to determine its properties for conferring improved wet adhesion to the paint composition into which the emulsion was incorporated.

The emulsion systems were prepared by mixing in a reaction vessel, a seed emulsion composed of:

| | pbw |
|---|---|
| (g) FLEXBOND 325 (55% solids) | 91. |

-continued

|  | pbw |
|---|---|
| Natrosal 25.0 LR (hydroxyethyl cellulose) | 0.89 |
| Fe++ | trace |
| Deionized water | 539 |

(g) A copolymer emulsion prepared from 86 parts vinyl acetate, 14 parts butyl acrylate, stabilized with hydroxyethyl cellulose. FLEXBOND is a registered trademark of Air Products and Chemicals, Inc.

The reactants were agitated at 200 RPM and heated to 65° C. while purging with nitrogen. There were simultaneously delayed to the emulsion seed over a 2 hour period, the following:

|  | pbw |
|---|---|
| Vinyl acetate | 868. |
| n-Butyl acrylate | 97. |
| Igepal CO 887 | 15. |
| Igepal CO 630 | 10.5 |
| Pluronic F 68 | 15.5 |
| Pluronic L 64 | 15.5 |
| t-Butyl hydroperoxide (70%) | 1.4 |
| Followed by a solution composed of Ureido or amide compound being tested | 0.75% by weight of monomers |
| Deionized water | 200 parts |

The polymerization temperature was maintained at 65° C. using an activator solution consisting of

|  | pbw |
|---|---|
| Discolite PEA | 0.4 |
| Sodium benzoate | 1.1 |
| Deionized water | 16.4 |

The vinyl acetate free monomer content was kept between 3–5% throughout the polymerization with a jacket temperature between 53°–65° C. At the end of the delays, and when the vinyl acetate-free monomer content was below 0.5%, the emulsion was cooled. The final pH was 5.1 and solids content were 55.6%.

TABLE 1

| Test Compound | Cut Film | |
|---|---|---|
|  | 1st cut 5,000 cycles | Recut 1,000 cycles |
| N-allyl urea | Pass | Pass |
| Allyl carbamate | Fails after 250 | Fails at 340 |
| β-Allyloxy propionamide | Fails at 100 | Fails at 239 |
| Compound of Formula VIIIc | Pass | Pass |
| Compound of Formula VIIIb | Fails | Pass |
| N-carbamyl maleamic acid | Fails | — |
| Compound of Formula VIIa | Pass | Pass |
| Compound of Formula IXc | Pass | Pass |
| 3-buteneamide | Fails | — |
| N-carboallyloxy urea | Fails | — |
| N-carboallyloxy ethyleneurea | Fails | — |
| N-(allyloxyacetyl) ethyleneurea | Fails | — |
| Control | Fails at 100 | Fails at 100 |

TABLE 2

| Test Compound | FLOATING BOARD % Removal to green paint | |
|---|---|---|
|  | Wet | Dry |
| N-allyl urea | 0 | 0 |
| Allyl carbamate | 26 | 4 |
| β-Allyloxy propionamide | 98 | 0 |
| Compound of Formula VIIIc | 1 | 0 |
| Compound of Formula VIIIb | 98 | 7 |
| N-carbamyl maleamic acid | 82 | 1 |
| Compound of Formula VIIa | 8 | 10 |
| Compound of Formula IXc | 16 | 4 |
| 3-buteneamide | 5 | 1 |

While the compound of Formula VIIIb failed to pass the 5000 cycle wet adhesion test, it did pass the 1000 cycle recut test, and therefore showed significant improvement over the control which failed both of these tests.

The novel ureido monomers of the invention can be incorporated into aqueous paint or coating formulations by interpolymerization in emulsions comprising acrylates or methacrylates, or in emulsions comprising vinyl ester systems which may contain one or more other unsaturated monomers. Thus, such systems may comprise vinyl acetate alone or in admixture with one or more monomers from among ethylene, vinyl chloride, maleic acid, and alkyl esters of acrylic, methacrylic and maleic acids. Such emulsion systems generally comprise, in addition to the polymerizable monomer or monomers free radical initiators and emulsifying, stabilizing, and surface active agents. Preferably, the activator comprises a redox system, typically made up of a peroxide or persulfate catalyst and a reducing component, such as an alkali metal formaldehyde bisulfite or sulfoxylate. The principal emulsifying agent is preferably one of the nonionic type and may also include surface active agents of the anionic type.

The novel ureido compounds of the invention, added to water-based flat exterior paints also impart improved resistance to blistering.

What is claimed:

1. A compound having the formula

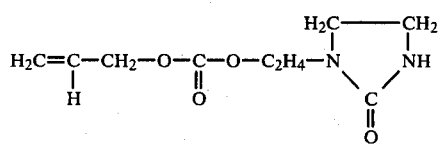

2. A compound having the formula

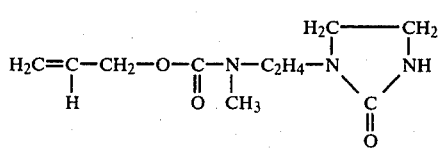

3. A compound having the formula

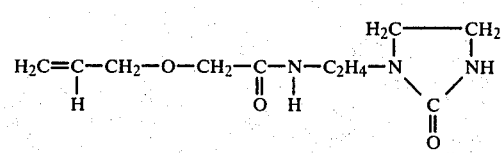

* * * * *